(12) United States Patent
Kilsgaard et al.

(10) Patent No.: US 8,923,542 B2
(45) Date of Patent: *Dec. 30, 2014

(54) TWO PART HEARING AID WITH DATABUS AND METHOD OF COMMUNICATING BETWEEN THE PARTS

(75) Inventors: Soren Kilsgaard, Smorum (DK); Preben Kidmose, Maarslet (DK); Mike Lind Rank, Farum (DK)

(73) Assignee: Widex A/S, Lynge (DK)

( * ) Notice: Subject to any disclaimer, the term of this patent is extended or adjusted under 35 U.S.C. 154(b) by 0 days.

This patent is subject to a terminal disclaimer.

(21) Appl. No.: 13/588,417

(22) Filed: Aug. 17, 2012

(65) Prior Publication Data

US 2013/0039519 A1    Feb. 14, 2013

Related U.S. Application Data

(63) Continuation-in-part of application No. PCT/EP2011/053515, filed on Mar. 9, 2011, and a continuation-in-part of application No. PCT/EP2010/052960, filed on Mar. 9, 2010.

(51) Int. Cl.
*H04R 25/00* (2006.01)
*A61B 5/00* (2006.01)
*A61B 5/0476* (2006.01)
*G06F 1/26* (2006.01)
*H02J 7/34* (2006.01)

(52) U.S. Cl.
CPC ............ *A61B 5/6817* (2013.01); *A61B 5/0476* (2013.01); *G06F 1/266* (2013.01); *H04R 25/60* (2013.01); *A61B 2560/0214* (2013.01); *A61B 2560/0219* (2013.01); *H02J 7/345* (2013.01); *H04R 2225/021* (2013.01); *H04R 2460/03* (2013.01)
USPC ............ 381/324; 381/323; 381/322; 381/312

(58) Field of Classification Search
CPC ...... H04R 25/00; H04R 25/55; H04R 25/556; H04R 25/60; H04R 25/608; H04R 25/65; H04R 2225/021
USPC .................. 381/312, 314, 323–324, 328, 330
See application file for complete search history.

(56) References Cited

U.S. PATENT DOCUMENTS 5,774,791 A * 6/1998 Strohallen et al. ........... 455/41.1
5,878,146 A   3/1999 Andersen
(Continued)

FOREIGN PATENT DOCUMENTS

EP    1671578 A1    6/2006
JP    2006-102260 A  4/2006
(Continued)

OTHER PUBLICATIONS

International Search Report and Written Opinion for PCT/EP2011/053515 dated Apr. 14, 2011.
(Continued)

*Primary Examiner* — Paul S Kim
*Assistant Examiner* — Sabrina Diaz
(74) *Attorney, Agent, or Firm* — Sughrue Mion, PLLC

(57) ABSTRACT

A hearing aid comprises a power supply, a microphone and a base part to be arranged outside the ear canal of a hearing aid user, and an ear plug part to be arranged in the ear canal of a hearing aid user. The ear plug part comprises a receiver for transmitting sound into the ear canal, and a transducer generating a signal to be transferred to said base part. A databus connects the ear plug part with the base part. The databus comprises two electrical wires adapted for transmission of signal to the receiver, and for transmission of signal from the transducer to the base part. The databus provides power supply either from the base part to the ear plug part, or, from the ear plug part to the base part. The invention further provides a method for communicating between two parts of a hearing aid.

20 Claims, 5 Drawing Sheets

(56) References Cited

U.S. PATENT DOCUMENTS

| | | |
|---|---|---|
| 7,057,496 B2 * | 6/2006 | Bateman et al. ............... 370/212 |
| 2004/0116151 A1 * | 6/2004 | Bosch et al. ............... 455/550.1 |
| 2006/0149330 A1 | 7/2006 | Mann et al. |
| 2007/0112277 A1 * | 5/2007 | Fischer et al. ................ 600/544 |
| 2007/0120715 A1 | 5/2007 | Zierhofer |
| 2009/0262964 A1 * | 10/2009 | Havenith et al. ............... 381/314 |

FOREIGN PATENT DOCUMENTS

| | | |
|---|---|---|
| WO | 2005076664 A1 | 8/2005 |
| WO | 2006047874 A1 | 5/2006 |
| WO | 2006066577 A1 | 6/2006 |
| WO | 2007047667 A2 | 4/2007 |
| WO | 2009100654 A1 | 8/2009 |

OTHER PUBLICATIONS

Office Action for counterpart Japanese Patent Application No. 2012-556500 dated Jan. 7, 2014 with English translation.

* cited by examiner

TWO PART HEARING AID WITH DATABUS AND METHOD OF COMMUNICATING BETWEEN THE PARTS

RELATED APPLICATIONS

The present application is a continuation-in-part of application PCT/EP2011053515, filed on Mar. 9, 2011, in Europe and published as WO 2011/110579 A1. The present application is a continuation-in-part of application PCT/EP2010/052960, filed on Mar. 9, 2010, in Europe and published as WO 2011/110218 A1

BACKGROUND OF THE INVENTION

1. Field of the Invention

The present invention relates to hearing aids. The invention further relates to a hearing aid in two parts connected with electrical wires. The invention more specifically concerns a hearing aid having a base part to be arranged outside the ear canal of a hearing aid user, and an ear plug part to be arranged in the ear canal of a hearing aid user. The invention further relates to a method for communicating between two parts of a hearing aid.

A hearing aid is an electronic portable device adapted to compensate a hearing deficit of a user by a microphone, amplifier and a receiver. Many types of hearing aids are made as a two part device with one part, an ear plug or ear piece, for being arranged in the ear canal of the hearing aid user, and another part, a base part, for being arranged outside the ear canal. Often the base part is arranged behind the ear, known as a behind-the-ear housing. The base part will usually comprise signal processing means, one or two microphones, and a battery. In modern hearing aids the receiver is often arranged in the ear plug part and connected with the signal processing means in the base part through electric wires. This type is sometimes referred to as a Receiver-In-The-Ear (RITE) hearing aid.

It is often suggested to arrange different transducers in the ear plug part. One example is a microphone in the ear plug, at the side proximally to the tympanic membrane, for transforming sounds in the ear canal into electrical signals. Such a microphone may have many purposes during fitting and during daily use of the hearing aid. Also, a temperature sensor, an accelerometer and EEG measuring electrodes are considered as transducers which could be relevant to arrange in the ear plug part. The electrical signal from such a transducer needs to be transferred to the signal processing means of the base part of the hearing aid, normally by an extra pair of wires, for further processing, e.g. input to acoustic processing, logging or transmission to a remote device. It has now been realized that one problem in having such a transducer, e.g. a microphone, is that the wires used for transferring the signal from the transducer to the base part may pick up electromagnetic interference. The electrical signal generated in a microphone may be relatively weak, e.g. 1-5 µV, and therefore rather sensitive to noise.

It has also now been realized that this problem is larger when a receiver is arranged in the ear plug, since the wires supplying the receiver signal, which may be 2 V at peak level, will be arranged close to the wires transferring the signal from a transducer. Therefore, there may be a risk that the receiver signal will induce noise into the wires carrying the transducer signal.

2. The Prior Art

US-A1-2004/0116151 describes a databus which can also be applied for a hearing aid between a base part and a peripheral component. This databus is described as needing transfer of power, clock and synchronization signal.

One problem is that the number of wires should be as low as possible in order to keep the total diameter of the bundle of wires connecting the two parts as small as possible. Each wire is connected both to the ear plug part and to the base part, e.g. through a connector. This connection will take up some space, and will in general be a weak point in the construction, i.e. there is a risk of losing the electrical connection at this point. Furthermore the connectors typically applied are relatively expensive components. Therefore, keeping the necessary number of connections to a minimum is to be preferred.

SUMMARY OF THE INVENTION

In a first aspect, the invention provides a hearing aid comprising power supply means and at least one microphone for transforming an acoustic signal in the surroundings of a hearing aid user into an electric signal, said hearing aid further comprising a base part to be arranged outside the ear canal of a hearing aid user, said base part comprising signal processing means, an ear plug part to be arranged in the ear canal of a hearing aid user, said ear plug part comprising a receiver for transmitting sound into the ear canal, said ear plug part comprising a transducer generating a signal to be transferred to said base part, and a databus connecting said ear plug part with said base part, said databus comprising two electrical wires adapted for transmission of a signal to said receiver, and for transmission of a signal from said transducer to said base part, and said databus being adapted for providing power supply either from the base part to the ear plug part, or, from the ear plug part to the base part, through said two electrical wires, wherein at least three different states of the databus are applied in different time slots, where a first state is for transfer of power, a second state is for transmission of signal from said base part to said ear plug part, and a third state is for transmission of signal from said ear plug part to said base part.

When separating in time the power transfer from the data transfer the risk of noise problems is reduced. The term different time slots refers to this separation in time of power transfer and data or signal transfer in both directions. At the same time the invention facilitates a two wire databus without the need of any further electrical wires.

A databus is here understood to be a digital communication line which can be set up for communication between different units, suitable for carrying signals in more than one direction. The databus is a serial databus, and is here also understood to be able to transfer power.

A transducer is here understood as a device which can transfer a physical parameter into an electrical signal in the hearing aid. This definition includes an electrode being able to read a voltage potential, such that the potential in some form can be transferred to the signal processing means of the hearing aid.

In an embodiment of a hearing aid according to the invention the transducer is an ear canal microphone for transforming an acoustic signal in the ear canal into an electric signal. Such a microphone, i.e. an internal microphone, will be advantageous during fitting, where it will be possible to detect the sound presented to the hearing aid user's eardrum directly. An internal microphone can also have advantages in daily use, e.g. for occlusion cancellation and active noise reduction.

The transducer could also be a microphone in the concha part of the ear, but attached to the ear plug part. Such a microphone would be for detecting sounds from the surroundings to be amplified by the hearing aid. A microphone in concha may provide a more natural sound impression than a microphone in a base part behind the ear.

In an embodiment of a hearing aid, a fourth state of the databus is added which is set to low, i.e. to "0", in order for the first state for power transfer to start with a rising edge. Such a rising edge occurring at a known place in the sequence is important in order to interpret the signal on the databus.

In an embodiment of a hearing aid, the power supply is arranged in the base part and a capacitor is arranged in the ear plug part, said capacitor adapted for being charged during said first state for transfer of power, and for supplying power in periods where no power is transmitted through the databus. There will typically be more space in the base part and therefore more room for a power supply, such as a battery.

In an embodiment of a hearing aid, the first state for transfer of power takes up at least 50%, preferably at least 70%, of the time on the databus. This has been found to result in a sufficiently small power loss and a not too large capacitor for supplying power in the rest of the time.

In an embodiment of a hearing aid, the receiver in the ear plug part is connected such that it will not draw any power in the time where data is transferred on the databus, but only in the time where power is transferred. This can be achieved by short-circuiting the receiver during the transfer of data. The advantage of this will be that the receiver will not need to draw power from a capacitor in the ear plug part during the time where there is no transfer of power from the base part. This means that the capacitor in the ear plug part can be made much smaller, since it will only need to supply power to the electronic circuit of the ear plug part. A smaller capacitor will also have smaller physical dimensions, whereby the ear plug part can be made smaller. There are possible variations of this embodiment, e.g. where the receiver draws power in a smaller part of the time where data is transferred.

In an embodiment of a hearing aid, the ear plug part comprises an electronic chip, i.e. an integrated circuit (IC), connected with the transducer, the chip or IC being connected with the databus. The chip is a space efficient way of collecting the necessary circuits, e.g. for handling the databus communication and power transfer. One circuit is a voltage regulator for the power supply of the ear canal microphone. Another circuit is an analogue to digital converter for converting an analogue signal from the transducer into a digital signal. This analogue to digital converter is often a sigma-delta converter.

In an embodiment of a hearing aid, a clock frequency generator is arranged in either the base part or in the ear plug part of the hearing aid, and wherein a clock frequency is regenerated, by a clock frequency regenerator in the part of the hearing aid without clock frequency generator. Preferably, this regenerated clock frequency is synchronized with the clock frequency of said clock frequency generator. Usually the clock frequency generator is arranged in the base part of the hearing aid, and often the synchronization is performed by a phase-locked loop.

In an embodiment of a hearing aid, the ear plug part comprises at least two electrodes on an external surface, said electrodes being arranged for having contact with the ear canal of the user in order to be able to detect electrical potentials from the hearing aid user, e.g. EEG signals. EEG signals may be applied for detection of different types of imminent seizures or for controlling the hearing aid, e.g. by adjusting the amplification according to a brainstem response.

In a further embodiment, the ear plug part is connected with a transducer for measuring a physical or physiological parameter. Such a transducer could be adapted for measuring temperature, blood pressure, movement e.g. acceleration, orientation, i.e. whether the person is lying down, electrical signals of the body, e.g. EEG. Preferably such transducer is connected to the electronic module of the ear plug part and is prepared for transferring data to the signal processing means in said base part through the serial databus. An appropriate transducer for detecting the correct placement of the ear plug part in the ear canal could also be applied. This could be a capacitive transducer.

In a second aspect, the invention provides a method for communicating between two parts of a hearing aid comprising power supply means and at least one microphone for transforming an acoustic signal in the surroundings of a hearing aid user into an electric signal, said method comprising arranging a base part outside the ear canal of a hearing aid user, said base part comprising signal processing means, arranging an ear plug part in the ear canal of the hearing aid user, said ear plug part comprising a receiver for transmitting sound into the ear canal, said ear plug part comprising a transducer generating a signal to be transferred to said base part, and connecting said ear plug part with said base part through a databus comprising two electrical wires adapted for transmission of signal to said receiver, and for transmission of signal from said transducer to said base part, and said databus being adapted for providing power supply either from the base part to the ear plug part, or, from the ear plug part to the base part, through said two electrical wires, applying at least three different states of the two wire databus sequentially in different time spans, where a first state is for transfer of power, a second state is for transmission of signals from said base part to said ear plug part, and a third state is for transmission of signal from said ear plug part to said base part.

In an embodiment of this method, at least three different states of the two wire databus apply sequentially in different time spans. A first state is for transfer of power, a second state is for transmission of signal from the base part to the ear plug part, and a third state is for transmission of signal from the ear plug part to the base part.

BRIEF DESCRIPTION OF THE DRAWINGS

Embodiments of the invention will now be explained in further detail with reference to the figures.

DETAILED DESCRIPTION OF THE INVENTION

Figure 1:
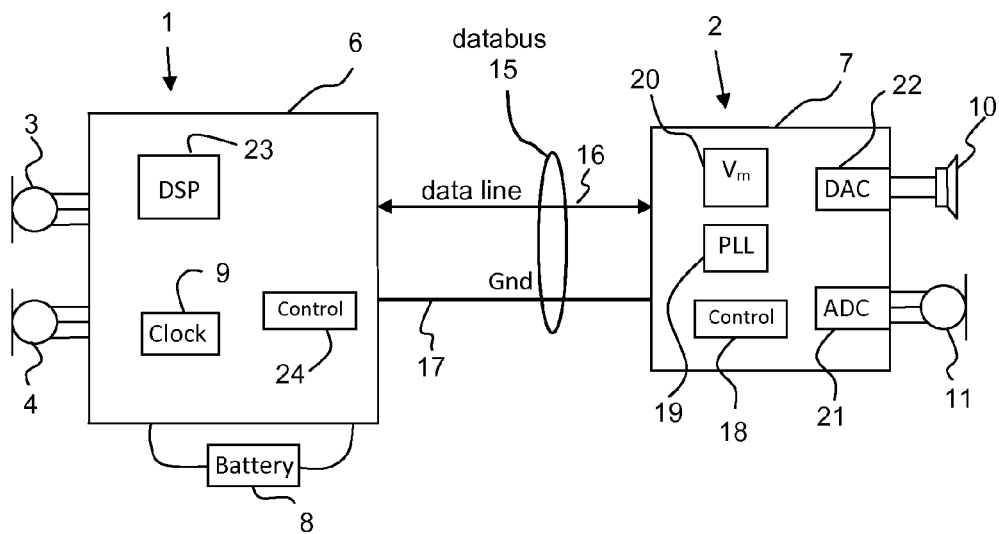
FIG. 1 illustrates an embodiment where a hearing aid is provided with a databus between the base part and the ear plug part.

FIG. 1 shows the principles of a hearing aid where the base part 1, often arranged behind the ear, comprises two microphones 3, 4, an electronic module 6, a receiver 10 and a battery 8. The electronic module 6 comprises signal processing means 23, a clock generator 9 and a controller 24 for controlling the communication on the data line 16. The ear plug part 2 of the hearing aid comprises an electronic module or electronic chip 7 and a microphone 11. The ear plug part 2 also comprises a receiver 10.

Figure 2:
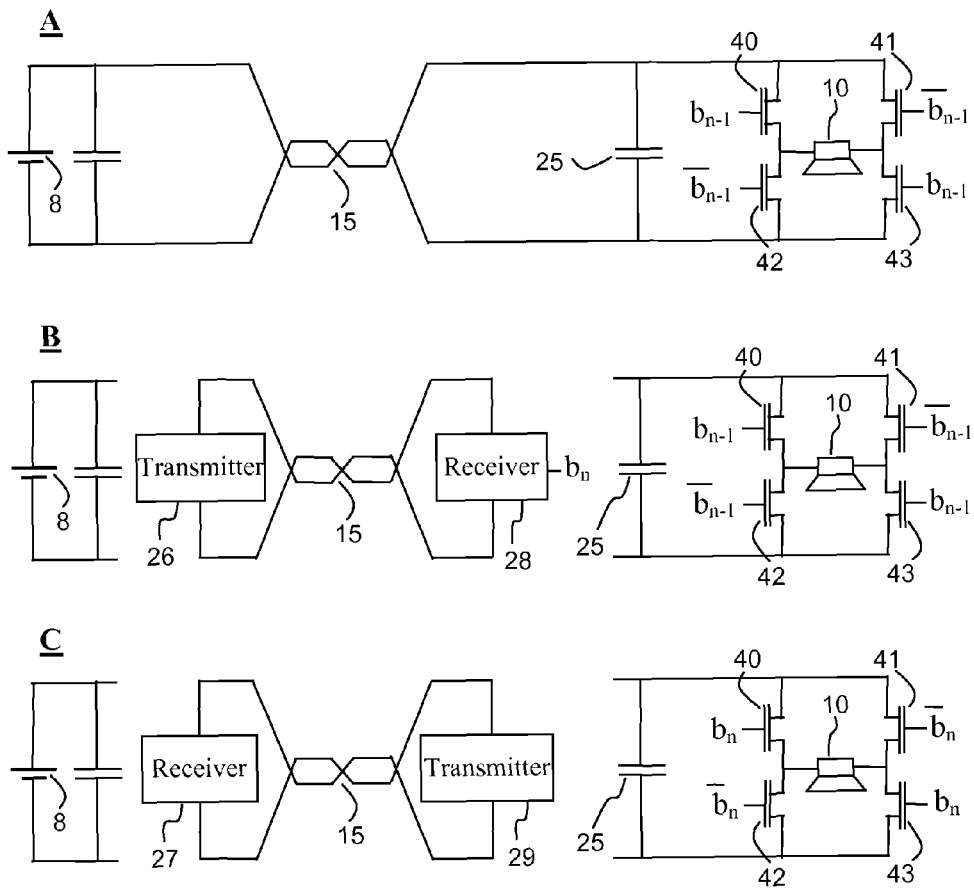
FIG. 2 illustrates the setup of a hearing aid in three different states of the databus.

The electronic module 7 of the ear plug part 2 may comprise a digital to analogue converter 22 for driving the receiver 10, and an analogue to digital converter 21 for digitizing the signal from a transducer, such as a microphone 11, near the tympanic membrane. The digital to analogue converters may be implemented in the form of delta sigma converters, known from U.S. Pat. No. 5,878,146. A delta sigma converter comprises a delta sigma modulator and a low pass filter. The delta sigma modulator may be arranged in the base part For driving the receiver an H-bridge may be applied. An H-bridge is described in WO-A1-2005/076664 and is also illustrated in FIG. 2.

The receiver 10 in the ear plug may be one single unit handling the whole frequency spectrum of interest. However, the receiver could also be composed of two separate receiver units, one for higher frequencies and one for lower frequencies. Both receiver units may be arranged in the ear plug part 2. Alternatively, the receiver unit for the lower frequencies could be arranged in the base part, 1 and the sound from this unit could be transmitted to the ear plug through a sound tube (not shown). The loss of low frequency sound in a sound tube is smaller than the loss of high frequency sound in a sound tube. Such an embodiment may be preferred for high power hearing aids where large receiver units are necessary in order to obtain sufficient sound pressure.

Two electrical wires 16, 17 or lines are connecting the base part with the ear plug part in the embodiment illustrated in FIG. 1. The two wires are for both the power supply and for the digital communication. A protocol is applied for controlling when power is transmitted and when data is transmitted in either direction on the serial databus. Different types of protocols may be applied for controlling the transmission.

The databus signal may also be sent as a balanced signal on a pair of wires. This will also reduce the risk of noise influencing the databus communication. A balanced pair of wires could be twisted in order to further reduce noise influence.

Usually the battery is arranged in the base part, and a voltage regulator is applied for supplying a stable voltage VDD for the electronic modules. The voltage transferred through the two wires as part of the protocol needs to charge a capacitor from which power is drawn during the data transmission on the databus. Often a local voltage regulator 20 in the ear plug part is provided.

FIG. 2 shows the three main states A, B and C of the databus. In the first state A the battery 8 in the base part 1 is connected through the databus 15, illustrated as a twisted two electrical wire connection, to the ear plug part 2, where the supply voltage will charge the capacitor 25 and power the sound output stage, i.e. the switches 40, 41, 42, 43 in the H-bridge and the receiver 10, e.g. through a voltage regulator. Switches (not shown) in both the base part and in the ear plug part are applied for reconnecting the circuit into the B state in FIG. 2. In this state the power supply to the ear plug is disconnected. Instead a transmitter 26 in the base part is connected through the databus 15 to a data receiver 28 in the ear plug part. During the B state data is transferred from the transmitter 26 to the data receiver 28. Typically, one bit is transferred during each B state period.

The one or more bit transferred in the B state sets the conditions for the four switches 40, 41, 42, 43 in the H-bridge in the time during other states until a new bit or bits have been transferred in the next B state. The data receiver 28 should be connected to control logic (not shown) for controlling the switches 40, 41, 42, 43 in the H-bridge. The control logic will hold the input to the switches until new data have been received. If more than one bit is transferred to the ear plug in each B state, the control logic should be set up for storing these bits and for presenting the correct bit to the input of the switches 40, 41, 42, 43 at the appropriate time during the time from one B state to the next.

In an example indicated in FIG. 2, $b_n$ is the level of the one bit transmitted to the data receiver 28 in the B state. The level $b_n$ is stored by the control logic, and when shifting from B state to the following C state, the control logic will shift the input on the switches 40, 41, 42, 43 from $b_{n-1}$ to $b_n$. This input $b_n$ will be held until the end of the next B state where it is shifted to $b_{n+1}$. The input $b_{n-1}$ to the switches 40, 41, 42, 43 was transmitted to the data receiver 28 in the B state previous to the one shown in FIG. 2.

As illustrated in FIG. 2 the switches 40, 41, 42, 43 in the H-bridge are switched to be open in one diagonal (e.g. 40 and 43) and close in the other one (e.g.) (41 and 42). This will open for current through the coil of the receiver in one direction. When the diagonal where the switches 40, 41, 42, 43 are open changes, the direction of the current, and thereby the movement of the membrane, also changes.

The last state shown in FIG. 2 is the C state following the B state when switches (not shown) in both the base part and in the ear plug part are applied for reconnecting the circuit into the C state. In the C state a transmitter 29 in the ear plug part 2 transmits one or more bits through the databus 15 to a data receiver 27 in the base part. These data transmitted out of the ear plug part could be data obtained from a transducer, such as a microphone 11, in the ear plug part. The data from the transducer will be digitized by an A/D converter 21 and packed for transmission in a control unit 18 in the ear plug part.

A further D state where a low bit or a "0" is sent on the databus is often following the C state, in order to initiate the A state with a rising edge. Such a rising edge is used for synchronization between the base part and the ear plug part as described below.

The capacitor 25 will be the power source to the receiver, H-bridge and other power demanding circuits in the ear plug part during the B, C and D states where no power, but only data, is transferred through the databus 15. The voltage regulator 20 (see FIG. 1) will ensure that the correct voltage is provided in all states. The databus 15 will thus face a relatively low impedance in the A state. In the B state the transmitter 26 will have a low output impedance whereas the data receiver 28 will have a high impedance. In the C state the transmitter 29 will have a low output impedance whereas the data receiver 27 will have a high input impedance.

In practice the capacitor 25 may be implemented as two capacitors in parallel (not shown). This would facilitate that one of these two capacitors could be applied for providing power supply to the H-bridge in the B and C state, and the other one of these two capacitors could be applied for providing power supply to either the receiver 28 in the B state or to the transmitter 29 in the C state.

In an embodiment where the receiver 10 or speaker is connected such that it will not draw any power in the time where data is transferred on the databus, but only in the time where power is transferred, the four switches 40, 41, 42, 43 in the H-bridge should be operated differently. The control logic controlling the switches 40, 41, 42, 43 in the H-bridge will then hold the input to the switches as described above only in the state where power is transferred, i.e. state A in the example. In the other states the receiver 10 could be short circuited in order not to draw any power from the capacitor 25. Short circuiting the receiver 10 may be achieved by opening switches 40, 41 simultaneously and closing switches 42, 43 simultaneously. It could also be opposite, i.e. closing switches 40, 41 and opening switches 42, 43.

Figure 3:
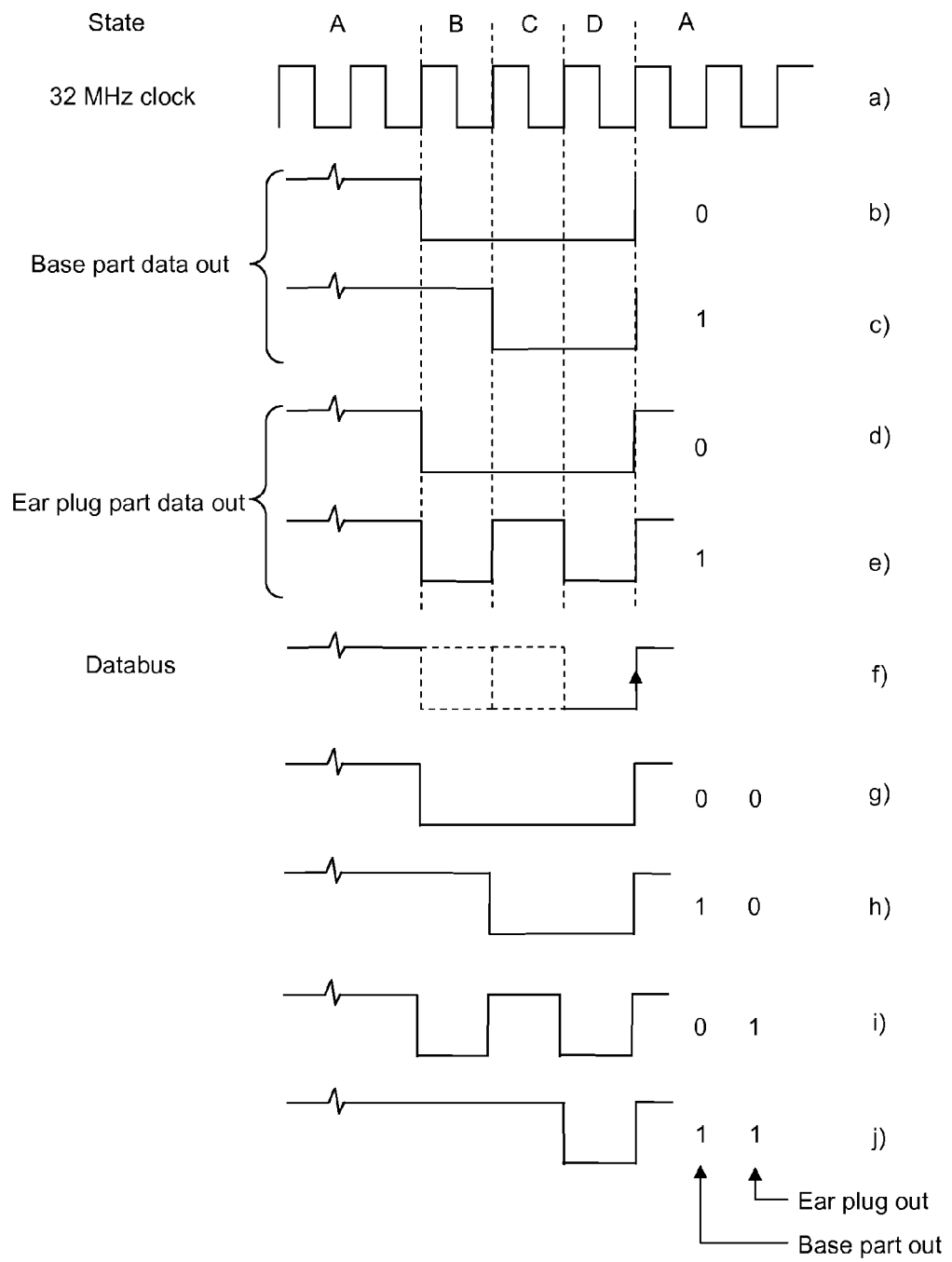
FIG. 3 illustrates the bidirectional digital communication through a databus, panes (a) through (k) signifying respective signals.
Figure 4:
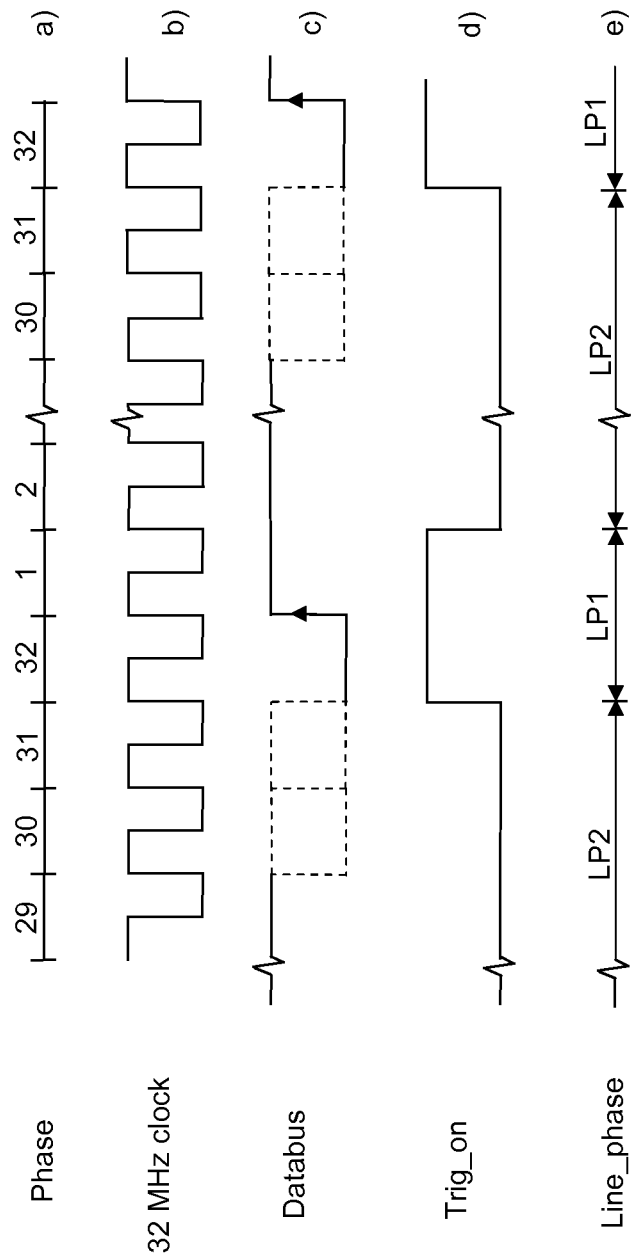
FIG. 4 illustrates different states for controlling the bidirectional digital communication, panes (a) through (e) signifying respective signals.

FIGS. 3 and 4 shows one example on how the power supply and the communication through a two wire bidirectional serial databus 15 could be handled. In FIG. 3 pane a, a 32 MHz clock frequency generated in the base part 1 is shown. A corresponding 32 MHz clock frequency is generated in the ear plug part 2 by application of a phase-locked loop (PLL) circuit 19 (see FIG. 5). The PLL 19 regenerates the 32 MHz clock frequency by application of the databus signal. The PLL continuously adjusts the synchronization between the two 32 MHz clock frequencies, by application of rising edges in the data line signal. When the clock generator 9 is arranged in the base part, as in this example, the PLL is arranged in the ear plug part. This synchronization is important for the proper functioning of the communication between the base part and the ear plug part.

The 32 MHz clock frequency is to be regarded as an example. Also other clock frequencies can be applied.

As illustrated in FIG. 3 pane a, the 32 MHz clock cycles can be divided into four different states (see top of FIG. 3) called A, B, C and D. In state A power is transferred, preferably from the base part to the ear plug part. In state B data is transferred from the base part to the ear plug. This would typically be the electrical signal to the receiver for the receiver to generate the acoustic signal. In state C data is transferred from the ear plug part to the base part. Such data is the digitized signal from one or more transducers in the ear plug. One transducer could be an internal microphone. The state D is always low or "0" such that the state A will start with a rising edge. This gives a rising edge for every cycle where the rising edges have a well defined time interval. These rising edges are then applied for synchronization of the clock frequency between the base part and the ear plug part. The order of the suggested states may be different. The state A could also be divided into two, or more, parts, separated by interchanging B and C states. It is also possible to add further states with other purposes in between the described states.

FIG. 3 panes b and c show an example on sending one bit from the base part to the ear plug part, where a "0" is sent in FIG. 3 pane b and a "1" is sent in FIG. 3 pane c. In both FIG. 3 pane b and in FIG. 3 pane c a "0" is sent out of the ear plug part.

FIG. 3 panes d and e show an example on sending one bit from the ear plug part to the base part, where a "0" is sent in pane d and a "1" is sent in pane e. In both FIG. 3 panes d and e, a "0" is sent out of the base part.

FIG. 3 pane f shows the resulting signal on the bidirectional databus, where the dashed lines indicate that the signal can follow one of the two possible routes, resulting in either a "0" or a "1" being sent. This resulting signal on the databus is a summation of signals from FIG. 3 pane b or c, and FIG. 3 pane d or e. In the example there will be a rising edge, indicated by an arrow in FIG. 3 pane f, in the databus signal for every 32 rising edges in the 32 MHz clock frequency. This means that the signal on the databus must go low before this rising edge, which is also the case in the databus signal shown in FIG. 3 pane f, due to the D state. A change in the databus signal level only occurs on rising edges of the 32 MHz clock frequency.

The mentioned rising edges in the data line signal, indicated with an arrow in FIG. 3 pane f, are applied for the PLL to synchronize the clock signals between the base part and the ear plug part.

FIG. 4 shows signals applied in the synchronization of the clock frequency. FIG. 4 pane a further illustrates the counting of phases by a phase counter. A phase counter is present in both the base part and in the ear plug part. The phase counter is part of a control means 18 of the ear plug part. The two phase counters are synchronized by the PLL via rising edges on the databus. The phase counter starts on 1 on a rising edge of the databus signal and increments by one for each rising edge on the 32 MHz clock until 32. After 32 the phase counter starts from 1 again. The phase counters could also be incremented by half by identifying the falling edges on the 32 MHz clock.

The phase counters are applied for identifying the states A where power is to be transferred, and the states B and C where either the base part or the ear plug part is sending data out.

FIG. 4 pane b repeats the 32 MHz clock frequency, and FIG. 4 pane c repeats the databus signal, both for ease of comparison in FIG. 4. It is seen from FIGS. 3 and 4 that the state A is active in the phase 1-29, the state B is active in the phase 30, the state C is active in the phase 31 and the state D, where a "0" is transmitted, is active in the phase 32. The phase count is also applied for shifting between the different setups illustrated in FIG. 2 for the different states. The different phases with the different states are regarded as different time slots.

The rising edge between the state D and the state A is intended for synchronization of the clock frequency in the base part and in the ear plug part. This rising edge is illustrated with arrows in FIG. 3 pane f and in FIG. 4 pane c. A different rising edge will occur between state B and C every time a "0" is sent out of the base part followed by a "1" sent out of the ear plug part. In order to discriminate between these two rising edges, the control unit 18 of the electronic module 7 of the ear plug part 2 is arranged for generating a signal to be applied for this discrimination. This signal is called Trig_on and is illustrated in FIG. 4 pane d.

The Trig_on signal is set to "1" (or high), when the phase equals 32 or 1. The Trig_on signal is set to "0" (or low), when the phase is from 2 to 31. At least Trig_on should be low in phase 30 and 31.

Figure 5:
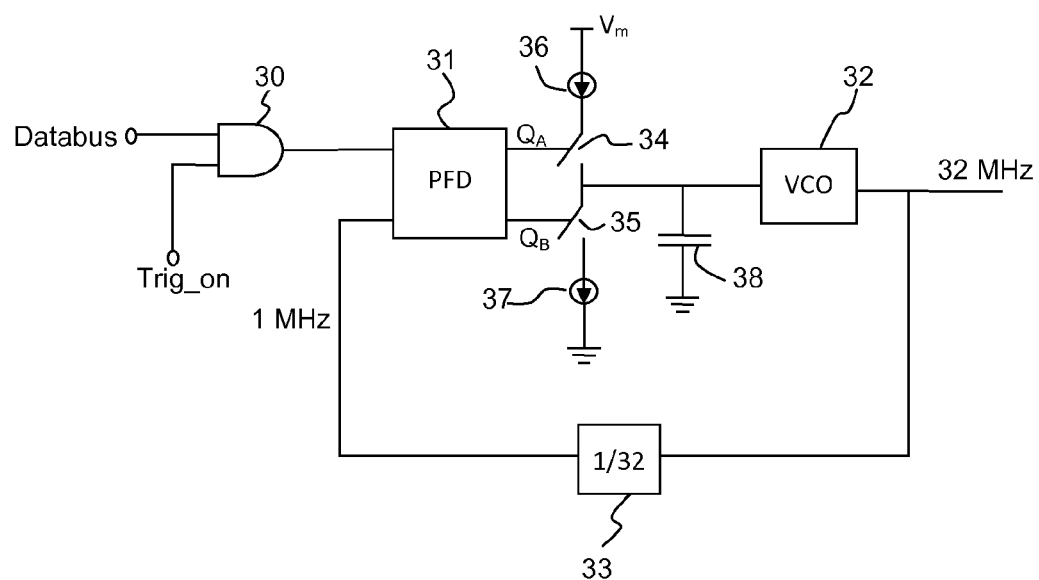
FIG. 5 illustrates a phase locked loop circuit applied in an embodiment of the invention.

FIG. 5 shows an example of the phase locked loop (PLL) circuit 19 applied for synchronizing the 32 MHz clock frequency between the base part and the ear plug part by application of rising edges marked with arrows in FIG. 3 pane f and FIG. 4 pane c. The data line signal goes to an AND operator 30 together with the Trig_on signal. The output of the AND operator 30 will thus only go high for the rising edges of the data line signal, marked with an arrow, and not for the rising edge when a "0" is sent out of the base part followed by a "1" sent out of the ear plug part (see FIG. 4 pane c and d). This is because the Trig_on signal is high at the data line rising edge marked with an arrow, while it is low when sending signal bits out of the base part or out of the ear plug part.

The signal from the AND operator 30 is the reference input to the phase frequency detector (PFD) 31. The other input to the PFD 31 is the feedback from the voltage controlled oscillator (VCO) 32 through a divider 33. The two outputs QA and QB of the PFD 31 control a first switch 34 and a second switch 35 through a train of pulses. A first constant current generator 36 and a second constant current generator 37 will either charge or discharge a capacitor 38, thereby determining the input voltage to the VCO 32. The two current generators 36, 37 usually generate the same current. A pulse on QA will close the first switch 34 connected with QA, whereby the first constant current generator 36 will be charging the capacitor 38. A pulse on QB will close the second switch 35 connected with QB, whereby the second constant current generator 37 will be discharging the capacitor 38.

When the two signals on the inputs of the PFD 31 are synchronized or locked, the length of the pulses QA and QB are the same and the voltage on the VCO 32 input remains unchanged. If the two signals on the inputs of the PFD 31 are out of synchronization, the pulses on one of the outputs QA and QB of the PFD 31 become longer than the pulses on the other output, thereby either charging or discharging the capacitor 38. This will adjust the input voltage on the VCO 32 to a level where the output frequency of the VCO is synchronized with the databus signal.

When starting up the bidirectional databus, e.g. when turning on the hearing aid, or when resetting the databus, the controller 18 should wait for the PLL to lock, i.e. for the two 32 MHZ frequencies to become synchronized. This is the case when the length of the pulses QA and QB are the same or approximately the same. When this happens, the ear plug part will be waiting for a rising edge on the data line. When the controller 18 detects a rising edge on the data line, the phase counter is set to 1. From this point in time the phase counter will continue as shown in FIG. 4 pane a, and as described above. In order for this start up procedure to function properly, the situation in FIG. 3 pane i should be avoided, i.e. a "0" from the base part followed by a "1" from the ear plug part should be avoided during start up in order not to get any other rising edge which could disturb the synchronization. This means that the databus signal initially has to look like the signal in FIG. 3 panes g, h or j.

Resetting the databus, and subsequent application of the above start-up procedure, can be initialized if the connection at one or more lines or wires is temporarily lost. Such a temporary loss of connection can be detected by the control circuit 18 of the ear plug electronic module 7. This could be done by checking the voltage over the capacitor 38 in the PLL 19 (see FIG. 5). The rising edges of the databus signal stops, this voltage will fall towards zero, and when the control circuit 18 detects this, the ear plug part should stop sending data on the databus, and at the same time the above start-up procedure should be initialized. The control circuit 18 may also be set up for detecting any temporary loss of connection on the power supply wires.

A specific code may be applied for confirming that the clock frequencies are properly synchronized. This code, or a different code, could also be sent with specific time intervals to confirm that the communication is functioning as scheduled. If this code stops, or the time intervals are not properly followed, a reset procedure could also be initialized. Such code will need to be sent as part of the signals sent out of the base part or out of the ear plug part arranged at specific times in the sequence of data signals.

In the above example of the data communication, one cycle of the clock frequency is applied for sending one bit from the base part to the ear plug part and one bit from the ear plug part to the base part. The data communication could be arranged in many other ways. Other options within the embodiments of the invention could be to send e.g. 2 or 4 bits from the base part followed by the same, or a different, number of bits sent from the ear plug part to the base part. The advantage of only sending one bit at a time is that the capacitor needed in the ear plug part for holding the supply voltage can be relatively smaller since the time in which the supply voltage needs to be held, without the capacitor receiving extra charge, will be relatively shorter. The number of bits sent in each of the two directions does not have to be the same. This could depend on the needs of the databus and the one or more transducers in the ear plug part.

Also the clock frequency will influence the necessary size of the capacitor. With a 32 MHz clock frequency, power will be transferred in the fraction $29/32$ of time according to the example above where data is sent out of the base part at 1 Mbit/s and data is sent out of the ear plug part at 1 Mbit/s. This means that the capacitor 25 only needs to hold the supply voltage in $3/32$ of a microsecond. If the clock frequency was 4 MHz and the demands for data transfer were the same, the capacitor would need to hold the supply voltage for $3/4$ of a microsecond. At the same time power would only be transferred in the fraction $1/4$ of time. This means that the capacitor should be larger and that the current running through the databus while transferring power would need to be higher in order to supply the necessary charge.

A higher current during the power supply period, i.e. state A, will lead to a higher power loss compared to the power loss at a lower current.

When the time fraction where no power is transferred is increased, the size of the capacitor 25 needs to be increased, in order for the capacitor to hold enough charge to be able to supply power in the time without power supply. Larger capacity also means physical larger dimensions of the capacitor. Due to the limited space in an ear plug, a small capacitor, and thus a relatively high clock frequency, will often be preferred.

A higher frequency will, however, also lead to a higher dynamic efficiency loss in the p-n junctions of the control circuit. This power loss is caused by charging the capacitive load of logic gates. For the databus alone the actual frequency causing this power loss is lower than the clock frequency, since the databus will be on the same level during the cycles of the A state. The number of shifts between "0" and "1" will therefore often be considerably lower than the controlling clock frequency, i.e. 32 MHz in the example. Thereby, the dynamic efficiency loss is also reduced.

1 Mbit/s should be sufficient for supplying the receiver 10 with an electrical sound signal of the necessary quality. For a microphone 11 in the ear plug part 2 the signal is digitized by an A/D converter 21, and this may result in a signal of around 2 Mbit/s. This signal will usually be pre-processed in the ear plug part and thereby reduced to approximately 600 kbit/s. A signal at this rate can easily be transmitted through the databus of the above example. The preprocessing is a decimation of the signal by a reduction of the sampling frequency and a low pas filtering, whereby high frequency quantification noise is removed.

In the embodiment where the receiver 10 or speaker is connected such that it will not draw any power in the time where data is transferred on the databus, but only in the time where power is transferred, the maximum acoustic output power from the receiver 10 will be reduced slightly. In the example with a 32 MHz clock frequency where power is transferred in the fraction $29/32$ of the time the reduction in maximum acoustic output power from the receiver 10 will be $3/32$ or approximately 1 dB.

When adding further transducers to the ear plug part, where data needs to be transferred through the databus to the base part, further bandwidth of the databus is necessary. Depending on the type of these transducers the amount of data to transfer may vary significantly. If the transducer is a thermometer or an accelerometer for detection of movements, the necessary amount of data for transfer may be relatively limited, whereas when the transducer is one or several EEG signals more data need to be transferred, but still considerably less than is the case for a sound signal.

When a number of transducers are comprised in or connected with the ear plug part, the data from these may be collected by the electronic module 7 of the ear plug part and packaged into a format suitable for sending via the databus together with e.g. the digitized sound signal from a microphone 11.

We claim:

1. A hearing aid comprising power supply means and at least one microphone for transforming an acoustic signal in the surroundings of a hearing aid user into an electric signal, said hearing aid further comprising
- a base part to be arranged outside the ear canal of the hearing aid user, said base part comprising signal processing means,
- an ear plug part to be arranged in the ear canal of the hearing aid user, said ear plug part comprising a receiver for transmitting sound into the ear canal, said ear plug part comprising a transducer generating a signal to be transferred to said base part, and
- a databus connecting said ear plug part with said base part, said databus comprising two electrical wires adapted for transmission of a signal to said receiver, and for transmission of a signal from said transducer to said base part, and said databus being adapted for providing power supply either from the base part to the ear plug part, or, from the ear plug part to the base part, through said two electrical wires,
- wherein at least three different states of the databus are applied in different time slots, where a first state is for transfer of power, a second state is for transmission of signal from said base part to said ear plug part, and a third state is for transmission of signal from said ear plug part to said base part.

2. The hearing aid according to claim 1, wherein said transducer is an ear canal microphone for transforming an acoustic signal in the ear canal into an electric signal.

3. The hearing aid according to claim 1, further comprising a fourth state of said databus set to low in order for the first state to start with a rising edge.

4. The hearing aid according to claim 1, wherein said power supply is arranged in the base part, and a capacitor is arranged in the ear plug part, said capacitor being adapted for being charged during said first state for transfer of power, and for supplying power in periods where no power is transmitted through the databus.

5. The hearing aid according to claim 4, wherein said first state for transfer of power takes up at least 50%, preferably at least 70%, of the time on the databus.

6. The hearing aid according to claim 1, wherein said ear plug part comprises an electronic chip connected with the transducer, said chip being connected with said databus.

7. The hearing aid according to claim 6, wherein said electronic chip comprises a voltage regulator for the power supply of the transducer.

8. The hearing aid according to claim 6, wherein said electronic chip comprises an analogue to digital converter for converting an analogue signal from the transducer into a digital signal.

9. The hearing aid according to claim 8, wherein said analogue to digital converter is a sigma-delta converter.

10. The hearing aid according to claim 1, comprising a clock frequency generator arranged in either the base part or in the ear plug part of the hearing aid, and a clock frequency regenerator in the part of the hearing aid without clock frequency generator.

11. The hearing aid according to claim 10, wherein said clock frequency regenerator is synchronized with the clock frequency of said clock frequency generator.

12. The hearing aid according to claim 10, wherein said clock frequency generator is arranged in said base part of the hearing aid.

13. The hearing aid according to claim 11, wherein said synchronization is performed by a phase-locked loop.

14. The hearing aid according to claim 1, wherein the ear plug part comprises at least two electrodes on an external surface, said electrodes being arranged for contacting the ear canal of the user when inserting the ear plug in the ear canal, in order to detect electrical potentials from the hearing aid user, e.g. EEG signals.

15. The hearing aid according to claim 1, wherein said receiver is connected such that it will not draw any power in the time where data is transferred on the databus.

16. The hearing aid according to claim 1, wherein said databus includes only said two electrical wires.

17. The hearing aid according to claim 1, wherein said two electrical wires are the only wires connecting said ear plug part and said base part.

18. A method for communicating between two parts of a hearing aid comprising power supply means and at least one microphone for transforming an acoustic signal in the surroundings of a hearing aid user into an electric signal, said method comprising
- arranging a base part outside the ear canal of the hearing aid user, said base part comprising signal processing means,
- arranging an ear plug part in the ear canal of the hearing aid user, said ear plug part comprising a receiver for transmitting sound into the ear canal, said ear plug part comprising a transducer generating a signal to be transferred to said base part, and
- connecting said ear plug part with said base part through a databus comprising two electrical wires adapted for transmission of signal to said receiver, and for transmission of signal from said transducer to said base part, and said databus being adapted for providing power supply either from the base part to the ear plug part, or, from the ear plug part to the base part, through said two electrical wires,
- applying at least three different states of the two wire databus sequentially in different time spans, where a first state is for transfer of power, a second state is for transmission of signals from said base part to said ear plug part, and a third state is for transmission of signal from said ear plug part to said base part.

19. The method according to claim 18, wherein said databus includes only said two electrical wires.

20. The method according to claim 18, wherein said two electrical wires are the only wires connecting said ear plug part and said base part.

* * * * *